United States Patent
Olson et al.

(10) Patent No.: US 7,020,520 B2
(45) Date of Patent: Mar. 28, 2006

(54) DEFIBRILLATOR ENCLOSURE SYSTEM

(75) Inventors: Kenneth F. Olson, Edina, MN (US); Gene George O'Brien, Excelsior, MN (US)

(73) Assignee: Cardiac Science, Inc., Minneapolis, MN (US)

( * ) Notice: Subject to any disclaimer, the term of this patent is extended or adjusted under 35 U.S.C. 154(b) by 252 days.

(21) Appl. No.: 10/421,378

(22) Filed: Apr. 23, 2003

(65) Prior Publication Data
US 2004/0215241 A1    Oct. 28, 2004

(51) Int. Cl.
*A61N 1/365*    (2006.01)
(52) U.S. Cl. .......................................................... 607/5
(58) Field of Classification Search .................... 607/1, 607/5, 42; 600/300, 594; 169/23; 340/288, 340/289, 568.2; 200/61.62, 61.93
See application file for complete search history.

(56) References Cited

U.S. PATENT DOCUMENTS

| | | | |
|---|---|---|---|
| 3,893,095 A * | 7/1975 | DeJong | 169/23 |
| 6,301,501 B1 | 10/2001 | Cronin et al. | |
| 2004/0019258 A1 * | 1/2004 | Kavounas et al. | 600/300 |

* cited by examiner

Primary Examiner—George Manuel
(74) Attorney, Agent, or Firm—Patterson, Thuente, Skaar & Christensen, P.A.

(57) ABSTRACT

A defibrillator enclosure system generally includes an automated external defibrillator (AED), an openable cabinet, a detector, and an alarm circuit. The openable cabinet is used to enclose the AED while the detector monitors the presence and absence of the AED within the cabinet. Specifically, upon detecting that the AED is no longer within the cabinet, the detector activates an alarm circuit whereby an alarm indicating the absence of the AED is issued.

12 Claims, 7 Drawing Sheets

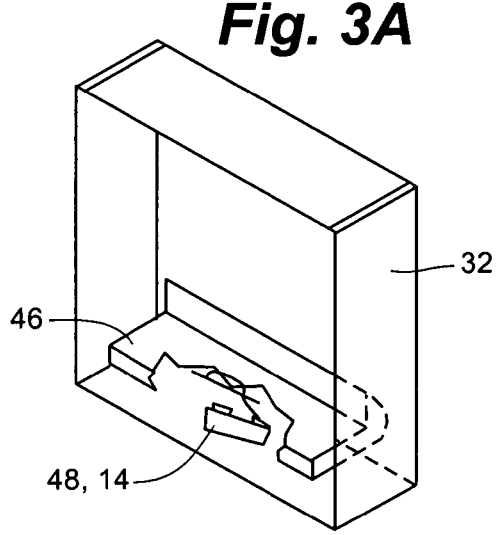
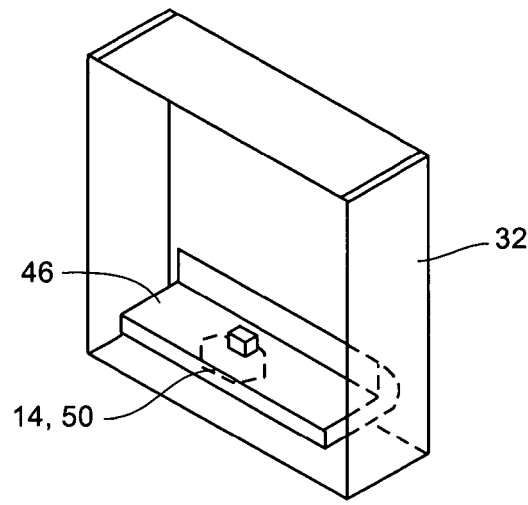
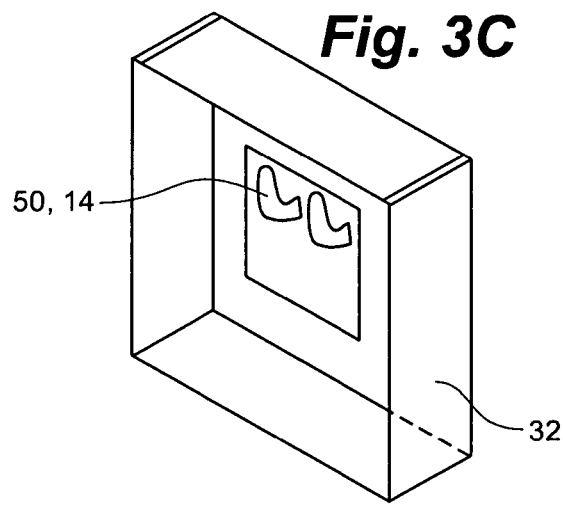
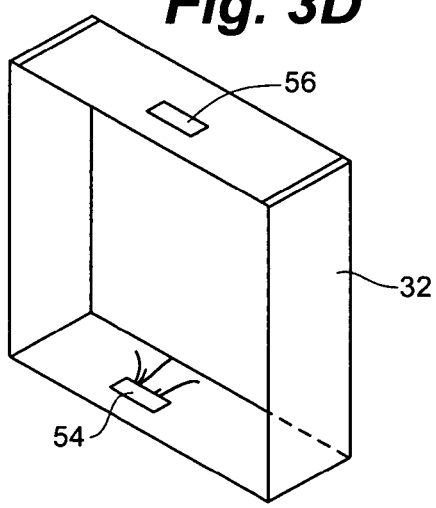
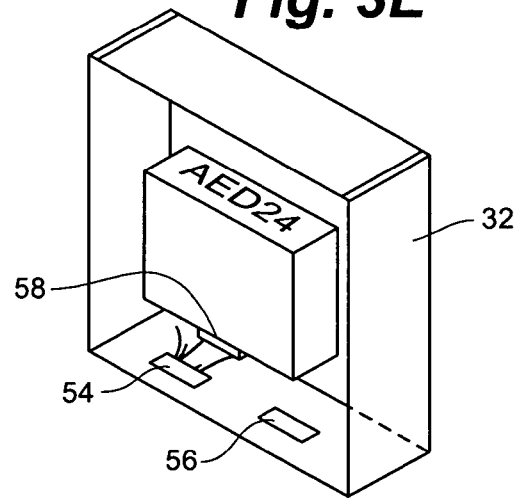

DEFIBRILLATOR ENCLOSURE SYSTEM

FIELD OF THE INVENTION

The present invention relates to an enclosure for an automatic external defibrillator (AED) and, more particularly, to an AED enclosure that provides an indicator that the AED has been removed from its enclosure.

BACKGROUND OF THE INVENTION

Automatic external defibrillators, or AEDs, are devices that in the past were typically accessible to only emergency personnel due to their cost. However, with improved technology and the decreasing costs of manufacture, AEDs are now becoming commonplace in locales frequented by the public, e.g., malls, sports arenas, schools, government buildings, airplanes, etc. Typically AEDs are fairly small, hand-portable devices that are used relatively infrequently. Consequently, they may be misplaced and not locatable by a rescuer unless presented in some form of an identifiable emergency cabinet akin to a fire extinguisher cabinet. The cabinet preferably provides some type of alarm indicating that an emergency situation is at hand so that others may become involved or obtain additional help for the situation at hand.

One such AED cabinet is described in U.S. Pat. No. 6,301,501. The cabinet provides a defibrillator mount that is connected to an interior surface of the cabinet so as to present the defibrillator in a position that allows a full view of the defibrillator through a window of the cabinet. The cabinet additionally provides for an audible and visual alarm that is connected to an exterior surface of the cabinet. These alarms are activated via a switch that detects when the door of the cabinet has been opened; an open door produces the alarms. A key switch that enables or disables the door switch is also provided. In the circuit of the '501 patent the alarm switch is constantly monitored causing the circuit to constantly consume battery energy. This significantly affects the life of the battery and the reliability of the alarms.

While the '501 patent provides a useful identifiable emergency cabinet, it provides one that activates an alarm only upon the cabinet door being opened and does not address the situation wherein the glass panel of the door has been broken and the AED removed, or the situation of a non-doored cabinet that provides only a breakable panel for access to the AED. Further, the AED cabinet of the '501 patent provides an alarm circuit that constantly draws power making battery life a significant concern in the use of this cabinet.

SUMMARY OF THE INVENTION

The limitations described above are in large part addressed by the defibrillator enclosure system of the present invention. The defibrillator enclosure system generally includes an automated external defibrillator (AED), an openable cabinet, a detector, and an alarm circuit. The openable cabinet is used to enclose the AED while the detector monitors the presence and absence of the AED within the cabinet. Specifically, upon detecting that the AED is no longer within the cabinet, the detector activates an alarm circuit whereby an alarm indicating the absence of the AED is issued.

Any number of devices may be used to detect the absence of the AED from the cabinet. These devices include but are not limited to a push button, a microswitch, a spring loaded bracket, and the combination of a light emitter/detector. The cabinet may be equipped with a shelf or bracket to support at least a portion of the weight of the AED; the shelf or bracket may also be used to present the AED in position so as to be viewable through a see-thru window in the cabinet enclosure. The alarm circuit is designed to be a no draw circuit, meaning it draws no power until the absence of the AED from the cabinet is detected by the detector, though this is not a requirement of this invention.

The present invention further includes a method for publicly securing an AED. The method includes the steps of: (1) fabricating an enclosure for the AED; (2) mounting the enclosure in a publicly accessible position; (3) enclosing the AED within the mounted enclosure; (4) monitoring the presence of the enclosed AED; and initiating an alarm upon the absence of the enclosed AED being detected.

BRIEF DESCRIPTION OF THE DRAWINGS

FIGS. 3A–3E depict alternative embodiments for alarm switches of the present invention.

DETAILED DESCRIPTION OF THE PREFERRED EMBODIMENTS

Figure 1:
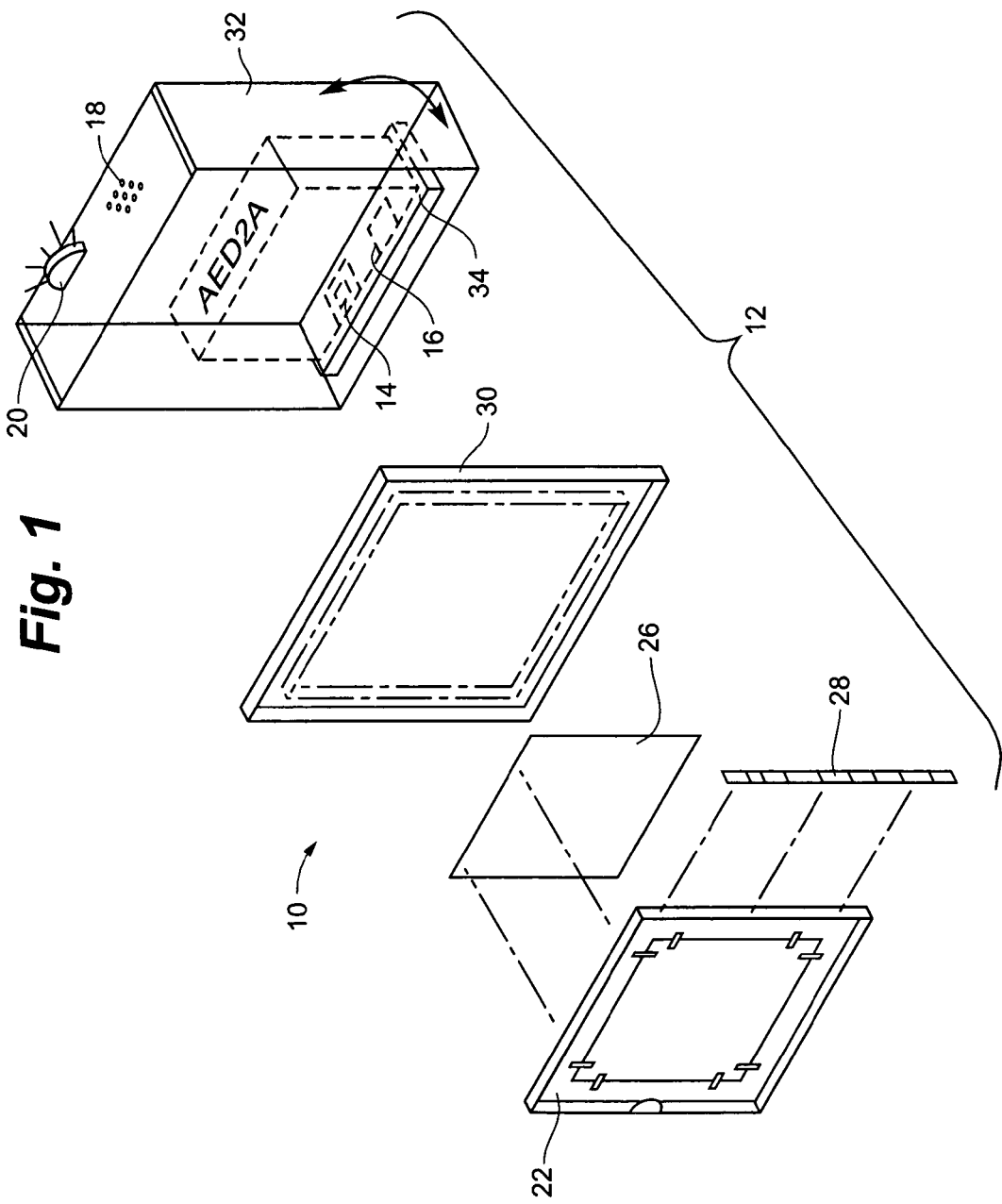
FIG. 1 depicts an automatic external defibrillator (AED) enclosure of the present invention.

The defibrillator enclosure system of the present invention provides an enclosure cabinet for an automatic external defibrillator (AED) that also includes an alarm circuit indicating when the AED has been removed from the cabinet. The alarm circuit of the defibrillator enclosure system draws power from a battery power source only upon the AED being removed from the cabinet. Referring to FIG. 1, the defibrillator enclosure system 10 of the present invention generally includes an enclosure cabinet 12, an alarm switch 14, an alarm circuit 16, an audible alarm 18 and/or a visible alarm 20.

In a preferred embodiment, the enclosure cabinet 12 includes a door 22 for access to the AED 24, however, the door 22 can be replaced with a breakable panel enabling access to the AED. The door 22 is preferably provided with a glass panel 26 enabling viewing of the AED 24 contained within the cabinet 12. A hinge 28 is preferably used to secure the door 22 to a faceplate 30 of the cabinet 12. The faceplate is secured to a five-sided box 32 completing the external coordination of the enclosure cabinet 12. In the embodiment of FIG. 1, the cabinet 12 is additionally provided with a spring-loaded pivoting shelf 34, the direction of pivot indicated by the arrows, upon which the AED 24 rests. The alarm switch 14 is positioned beneath the shelf 34 and activates upon the AED 24 being lifted from the shelf 34. The removal of the weight from the shelf 34 enables the shelf 34 to pivot upward such that the normally closed push button contact is open activating the alarm circuit 16.

Figure 2:
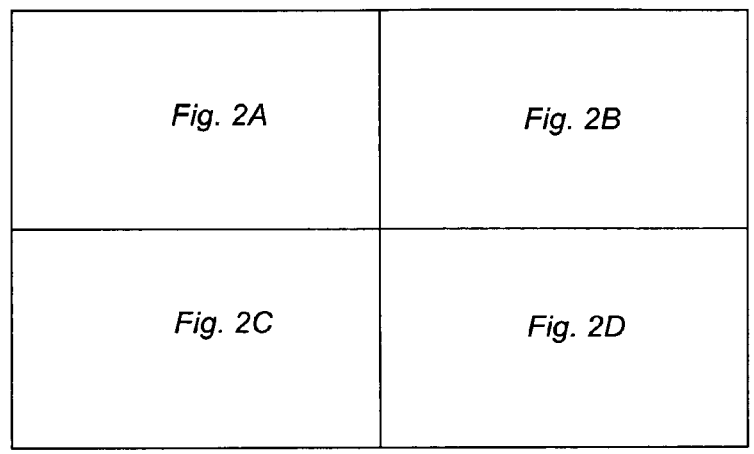
FIG. 2 is a circuit diagram of an alarm circuit of the present invention.
Figure 2A:
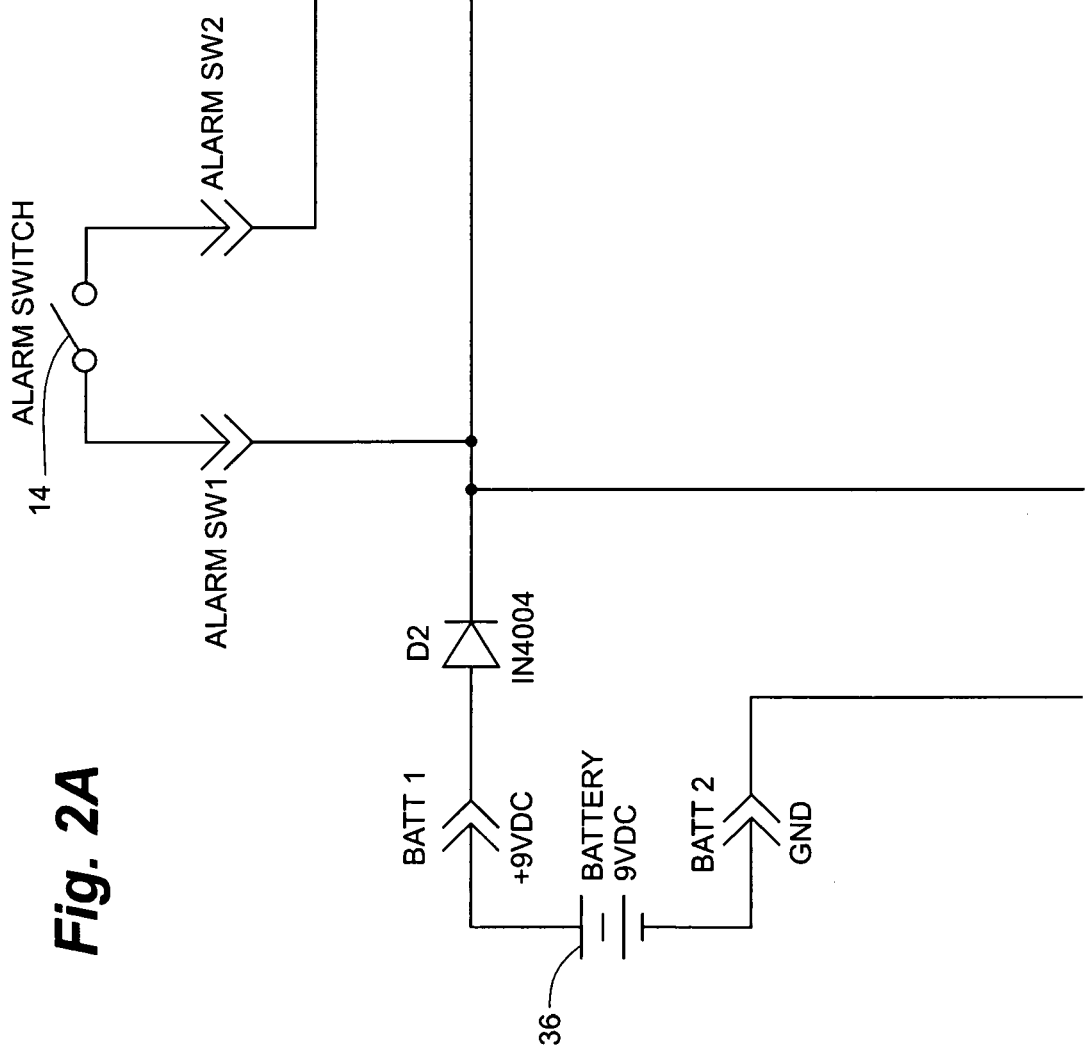
Figure 2B:
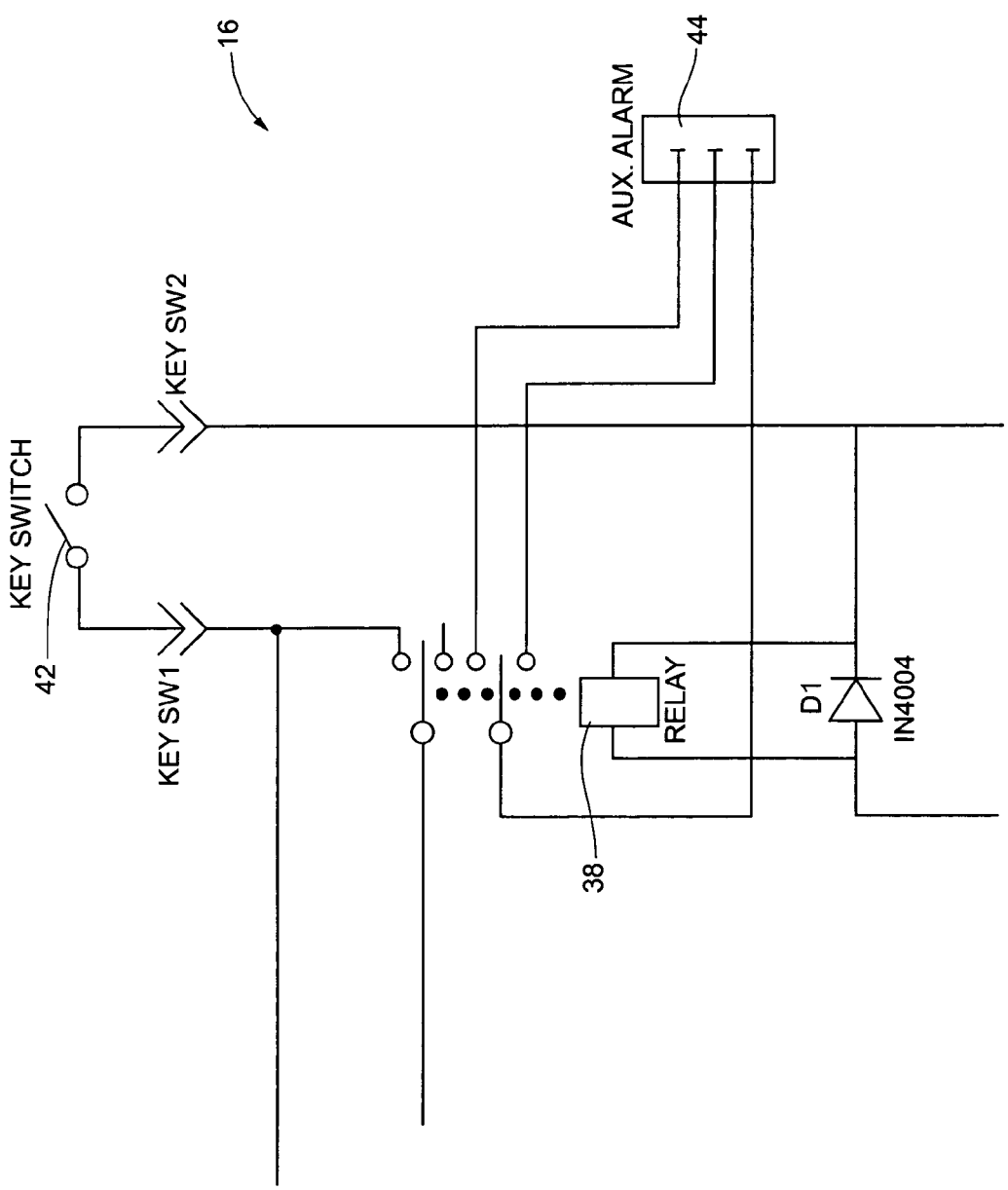
Figure 2C:
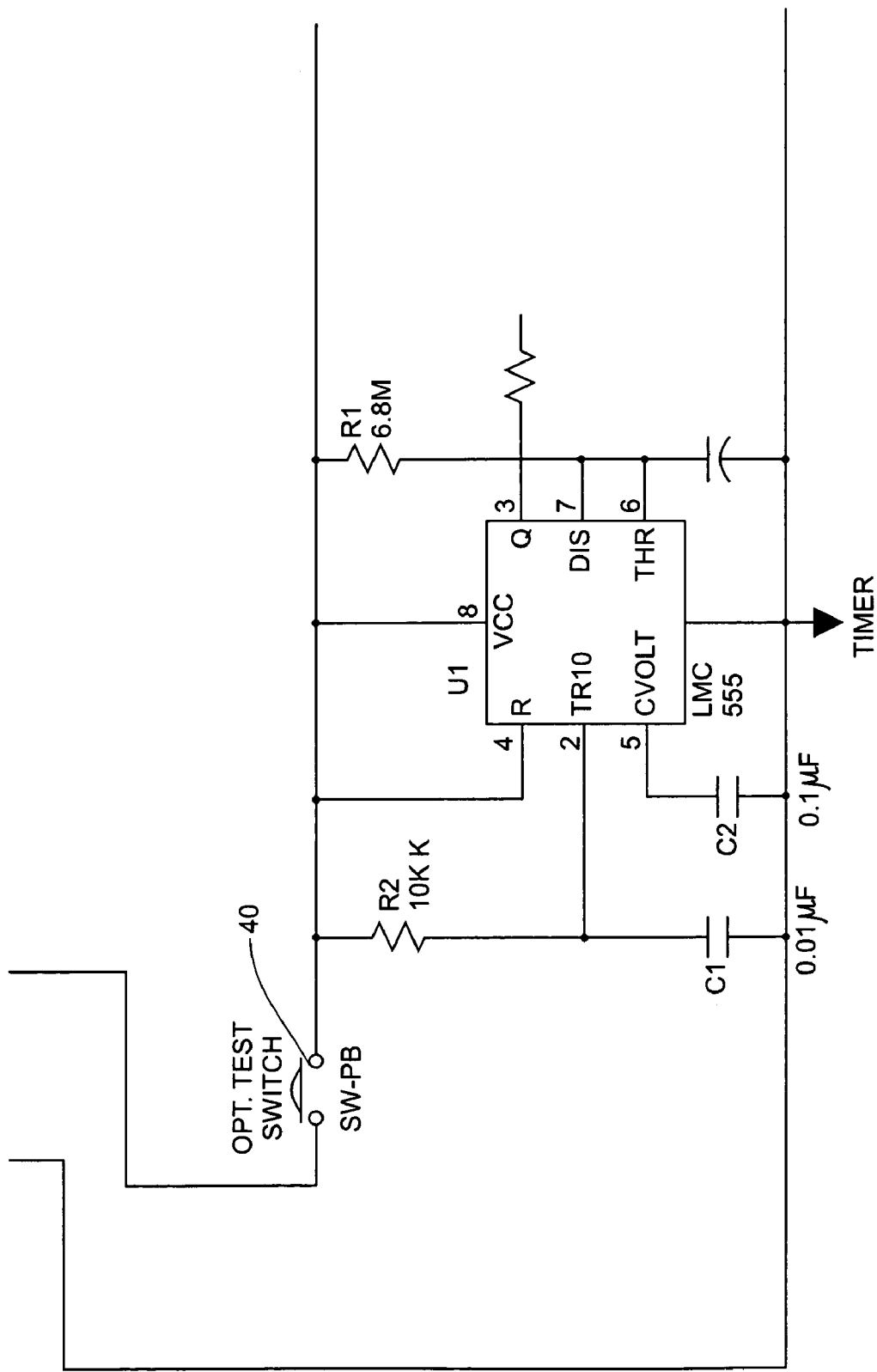
Figure 2D:
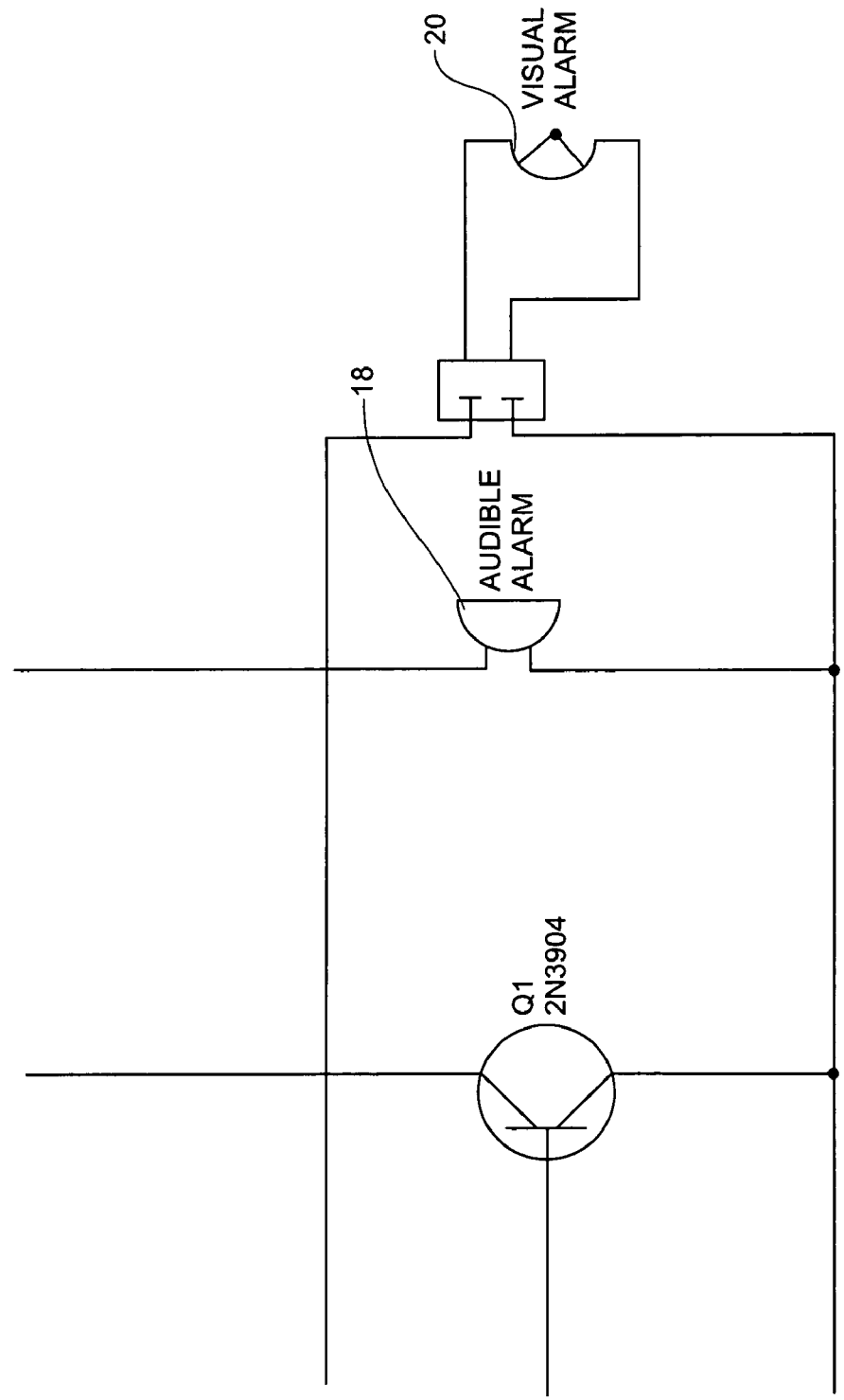

FIG. 2 depicts the alarm circuit 16. The alarm circuit 16 is designed to save battery energy, which is preferably provided by a nine-volt-DC battery 36. This is accomplished by not monitoring the alarm circuit 16, which is the common approach to alarm circuits and the one that is used in the '501 patent described in the Background of the Invention. Here, the alarm switch 14 is preferably a normally closed switch. As such, with the AED 24 in the cabinet 12, the alarm switch 14 is opened so that no current draw is put on the nine-volt battery, i.e., the contacts of the relay 38 are closed when the relay is de-energized. The alarm switch 14 is activated by the removal of the AED 24 from the cabinet that sounds the audible alarm 18 and/or the visual alarm 20, i.e., the contacts of the relay 38 are opened enabling a complete current path to the audible and/or visual alarm. Note that the alarm circuit 16 may additionally be provided with a test switch 40 for testing the alarms and a key switch 42 for enabling/disabling the alarms. A contact for activating an auxiliary alarm 44 may also be provided.

FIGS. 3A through 3E depict alternative embodiments to the pivoting shelf 34 and push button alarm switch configuration of FIG. 1. Specifically, FIG. 3A depicts a fixed shelf 46 within the five-sided box 32 of the cabinet 12 wherein a levered microswitch 48 (shown through use of a cut-away section of the shelf 46) extends through an opening in the shelf 46 and operates as alarm switch 14. The AED 24 (not shown) rests atop the microswitch 48 and shelf 46, removal of the AED from the shelf activating the alarm switch 14 and alarm circuit 16. FIG. 3B depicts the fixed shelf 46 with a push button 50 acting as the alarm switch 14. The push button 50 extends through an opening in the shelf 46 and operates similar to the microswitch 48 described immediately above.

FIG. 3C depicts an alternative embodiment of the present invention wherein the alarm switch 14 comprises a spring loaded hanging bracket 52, similar to an old-style telephone. The AED (not shown) is configured to hang from the spring-loaded bracket 52 wherein removal of the AED causes the bracket to spring upward and activate the alarm circuit 16. FIG. 3D depicts an alternative embodiment wherein the alarm switch 14 comprises a photoelectric beam emitter 54 and detector 56. Placement of the AED 24 (not shown) within the cabinet 12 blocks the beam of light preventing interception of the light by the detector 56 while removal of the AED enables the detector 56 to detect the light from the emitter 54 and activate the alarm circuit 16. The emitter 54 may be placed on a shelf upon which the AED sits or upon the bottom surface of the cabinet where the AED sits. FIG. 3E depicts an alternative embodiment wherein the alarm switch 14 comprises the emitter 54 and detector 56 in a side-by-side arrangement and comprises a light reflecting panel 58 on the AED 24. Upon lifting the AED 24 from the cabinet the light reflecting panel 58 reflects the light from the emitter 54 into the detector 56 thereby activating the alarm circuit 16. When the AED 24 is resting atop the emitter 54 and detector 56 no light is transferred between the two. The emitter 54 and detector 56 may be placed on a shelf upon which the AED sits or upon the bottom surface of the cabinet where the AED sits. Other manners of detecting removal of the AED from the cabinet 12 may be used without departing from the spirit or scope of the invention; the above-described alternative alarm switches are provided as examples and are not intended to limit the invention.

The concept of the defibrillator enclosure system is to provide a publicly accessible enclosure of an AED that also warns those around that the AED has been removed from the enclosure and an emergency is at hand. The defibrillator enclosure system provides these features when the enclosure is mounted in a publicly accessible position within a public location.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed:

1. A defibrillator enclosure system, comprising:
   an automated external defibrillator; and
   an enclosure having a spring-loaded pivoting shelf and an alarm switch, the spring-loaded pivoting shelf having a default bias to an upward position;
   wherein the automated external defibrillator resides on the spring-loaded pivoting shelf within the enclosure such that the spring-loaded pivoting shelf is in a downward position contacting the alarm switch; and
   wherein the alarm switch initiates a system alarm when the pivoting shelf is in the upward position.

2. The system of claim 1, wherein the alarm switch comprises a push button or a microswitch.

3. The system of claim 1, wherein said system alarm comprises an alarm circuit, wherein said alarm circuit draws power only upon the spring-loaded pivoting shelf assuming the upward position.

4. A defibrillator enclosure system, comprising:
   an automated external defibillator;
   an openable cabinet having a door and an internal pivoting shelf, wherein said openable cabinet encloses said automated external defibrillator such that the automated external defibrillator is viewable through a door panel;
   a detector, wherein the detector interfaces with the internal pivoting shelf to detect the absence of said automated external defibrillator within the openable cabinet; and
   an alarm circuit, wherein said alarm circuit is operably coupled to said detector and wherein said alarm circuit initiates an alarm upon said detector detecting the absence of said automated external defibrillator within said openable cabinet.

5. The system of claim 4, wherein said detector comprises a push button or a microswitch.

6. The system of claim 4, wherein said door comprises a viewing panel for observing the automated external defibrillator within the openable cabinet.

7. The system of claim 4, wherein said alarm circuit comprises a battery and wherein said alarm circuit draws power from the battery only upon the detection of the absence of said automated external defibrillator.

8. A defibrillator enclosure system, comprising:
   an automated external defibrillator;
   an openable cabinet having a pivoting shelf for holding the automated external defibrillator, wherein said openable cabinet encloses said automated external defibrillator;
   a detector positioned below the pivoting shelf, wherein the detector interfaces with the pivoting shelf to detect the absence of said automated external defibrillator within the openable cabinet; and
   an alarm circuit, wherein said alarm circuit is operably coupled to said detector and wherein said alarm circuit initiates an alarm upon said detector detecting the absence of said automated external defibrillator within said openable cabinet, and wherein said alarm circuit draws power only upon the detection of the absence of said automated external defibrillator.

9. The defibrillator enclosure system of claim 8, wherein the openable cabinet comprises a viewing panel for viewing the automated external defibrillator within the openable cabinet.

10. A method for publicly securing an automated external defibrillator, the method comprising the steps of:

fabricating an enclosure for said automated external defibrillator;
mounting said enclosure in a publicly accessible position;
positioning an upwardly biased shelf in a downward holding orientation;
positioning said automated external defibrillator on the upwardly biased shelf within said enclosure;
monitoring the presence of the enclosed automated external defibrillator on the upwardly biased shelf; and
initiating an alarm upon the absence from the upwardly biased shelf of the enclosed automated external defibrillator being detected through said monitoring.

11. The method of claim 9, wherein said step of monitoring is performed by a push button, a microswitch, a spring loaded bracket, or the combination of a light emitter and a light detector.

12. The method of claim 10, further comprising the step of maintaining said alarm in an unpowered state until the absence of the enclosed automated external defibrillator is detected.

* * * * *